(12) United States Patent
Mehdizadeh

(10) Patent No.: US 6,283,968 B1
(45) Date of Patent: Sep. 4, 2001

(54) POSTERIOR LAMINECTOMY PROCEDURE

(76) Inventor: Hamid M. Mehdizadeh, 14928 Diduca Way, Los Gatos, CA (US) 95032

( * ) Notice: Subject to any disclaimer, the term of this patent is extended or adjusted under 35 U.S.C. 154(b) by 0 days.

(21) Appl. No.: 09/519,284

(22) Filed: Mar. 7, 2000

(51) Int. Cl.⁷ .................................................... A61B 17/56
(52) U.S. Cl. ........................ 606/61; 623/17.16; 623/902
(58) Field of Search ............................. 128/898; 606/61; 623/17.16, 17.15, 17.11, 902

(56) References Cited

U.S. PATENT DOCUMENTS

| | | | |
|---|---|---|---|
| 3,848,601 | * 11/1974 | Ma et al. ............................. | 128/305 |
| 4,545,374 | * 10/1985 | Jacobson ............................. | 128/303 |
| 5,803,904 | * 9/1998 | Mehdizadeh ........................ | 600/235 |
| 5,961,522 | * 10/1999 | Mehdizadeh .......................... | 606/79 |
| 6,030,390 | * 2/2000 | Mehdizadeh .......................... | 606/84 |

* cited by examiner

Primary Examiner—Jeffrey A. Smith
Assistant Examiner—Eduardo C. Robert
(74) Attorney, Agent, or Firm—Henry M. Stanley

(57) ABSTRACT

A process is described for insertion of a prosthesis within an intradiscal space during a posterior laminectomy. The process insures proper orientation and alignment of prostheses inserted in the intradiscal space. The process also involves minimal removal of bone from the facet joint, which assures retention of the major portion of a patient's spinal column weight bearing capability.

7 Claims, 1 Drawing Sheet

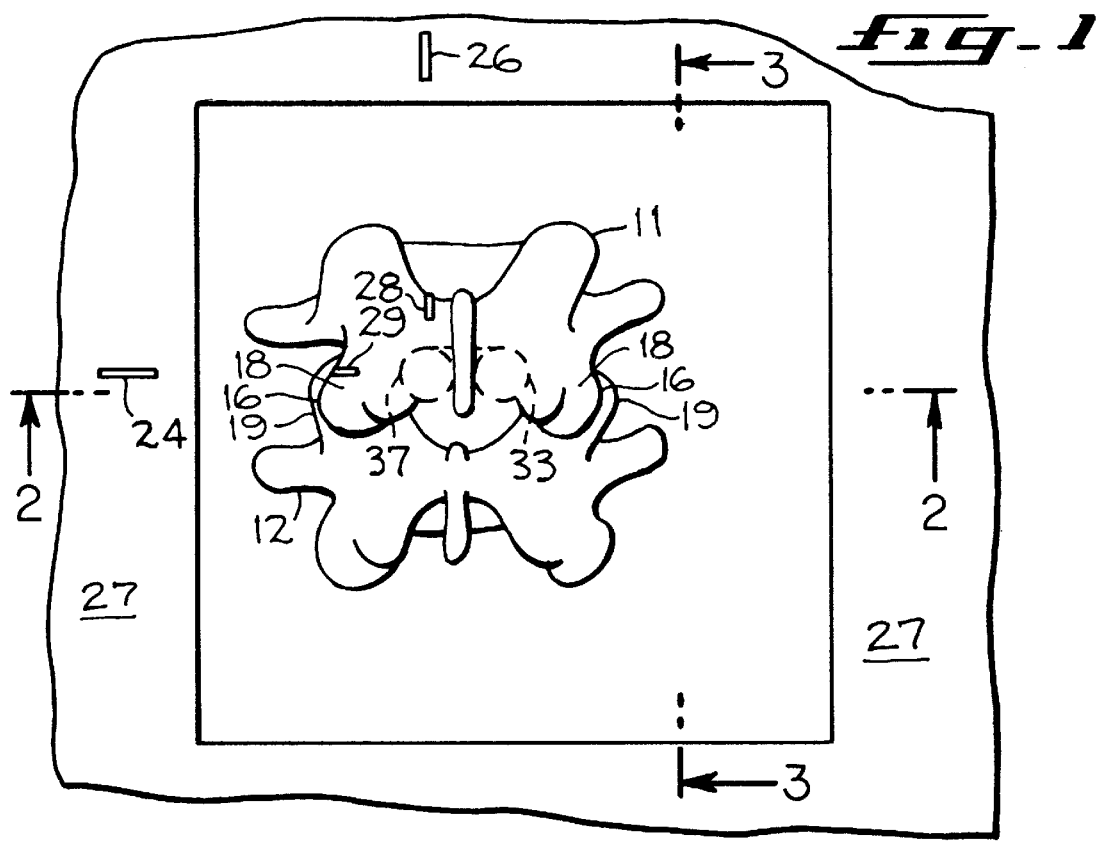
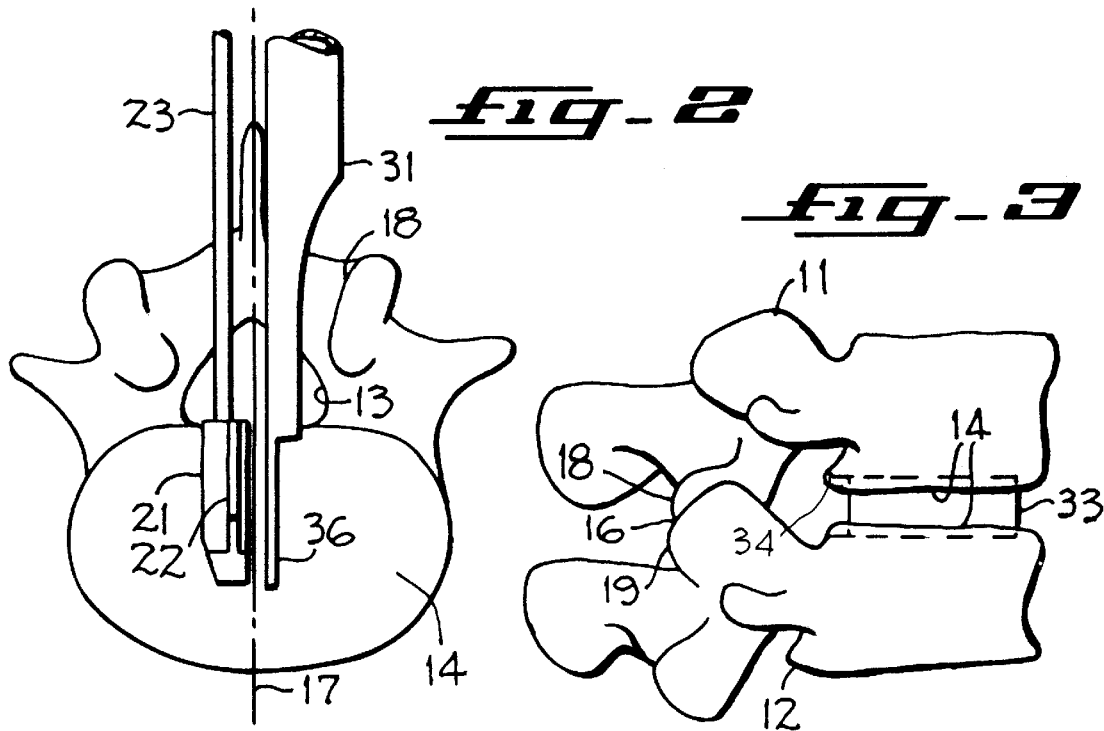

POSTERIOR LAMINECTOMY PROCEDURE

SUMMARY OF THE INVENTION

The invention disclosed herein is a posterior approach laminectomy procedure for placing a prosthesis within the intradiscal space between adjacent vertebrae. The procedure includes the steps of retracting the nerve root and the dural and inserting a disc space spreader within the intradiscal space. The direction of the disc space spreader insertion is recorded and a single tang retractor is inserted within the intradiscal space in a direction substantially parallel to the disc space spreader recorded direction. Further, the steps of forming the surfaces on the adjacent vertebrae to receive the prosthesis and positioning the prosthesis in contact with the formed surfaces using the single tang retractor as a guide are included.

A further aspect of the invention relates to a posterior approach laminectomy procedure for placing a prosthesis into the space between adjacent vertebrae which includes the steps of retracting the dural to an out of the way position and spreading the adjacent vertebrae. A single tang retractor is inserted into the space between the adjacent vertebrae and the direction of insertion of the single tang retractor is recorded. Opposing surfaces on the adjacent vertebrae are formed to receive the prosthesis using the single tang retractor as a guide. The prosthesis is positioned between the opposing surfaces along the single tang insertion direction.

In yet another aspect of the invention a posterior approach laminectomy procedure for placing a split prosthesis having a first half and a second half within the intradiscal space between adjacent vertebrae is disclosed. The halves of the split prosthesis are placed in positions on one side of and an opposite side of the spinal column center line. The procedure includes the steps of retracting the nerve root and dural and inserting a disc space spreader within the intradiscal space on the one side. The direction of the disc space spreader insertion is recorded and a single tang retractor is inserted within the intradiscal space on the opposite side in a direction substantially parallel to the disc space spreader recorded direction. Surfaces on the adjacent vertebrae are formed on the opposite side to receive the prosthesis second half The prosthesis second half is positioned in contact with the formed surfaces on the opposite side using the single tang retractor as a guide. The single tang retractor is removed from the opposite side and the disc space spreader is removed from the one side. The single tang retractor is inserted within the intradiscal space on the one side in the position vacated by the disc space spreader and substantially parallel with the disc space spreader recorded direction. The surfaces on the adjacent vertebrae on the one side are formed to receive the prosthesis first half. The prosthesis first half is positioned in contact with the formed surfaces on the one side using the single tang retractor as a guide. Thereafter, the single tang retractor is removed from the one side.

BRIEF DESCRIPTION OF THE DRAWINGS

FIG. 1 is a posterior view of the operating area surrounded by drapes.

FIG. 2 is a view along the line 2—2 of FIG. 1 wherein the view follows the lower surfaces of the superior vertebrae of FIG. 1.

FIG. 3 is a view along the line 3—3 of FIG. 1.

DESCRIPTION OF THE PREFERRED EMBODIMENTS

This procedure relates to laminectomy procedures in humans primarily in the lumbar region. The spinal column is the bony structure that runs along the back, represented in FIG. 1 by a pair of adjacent vertebrae, a superior vertebrae 11 and an inferior vertebrae 12. The dural is a column containing the nerve paths and for the sake of simplicity herein will include the nerve roots when reference is made to retraction of the dural. The dural runs within a channel seen as item 13 in FIG. 2 of the drawings and is not shown in the drawings for purposes of clarity. The back of the spinal column is seen in FIG. 1 and is that portion of the spinal column which provides the primary weight bearing structure. The front of the spinal column or that portion which is toward the abdomen, is seen in the lower portion of FIG. 2 providing the shock absorbing portion of the structure. The shock absorbing function is performed by discs which are situated between adjacent vertebrae bearing upon the relatively broad surfaces seen as item 14 in FIG. 2. The bony structure near the back of the spinal column has a facet joint 16 on each side of a center line 17 through the spinal column that joins an inferior vertebrae with a superior vertebrae through cartilage tissues. The facet joint contains an inferior facet 19 and a superior facet 18 as seen in FIG. 1. When it is necessary to reach the region of the surfaces 14 on the vertebrae during a posterior approach laminectomy procedure instruments and prostheses must pass the facet joints as can be seen with reference to FIGS. 1 and 2. One of the purposes of the procedure disclosed herein is to remove less bone and cartilage from the facet joint during laminectomies and another purpose is to provide greater freedom for the surgeon to orient the prostheses adjacent the surfaces 14 with greater accuracy.

Pre- and post-operative procedures during laminectomies are not subjects of the procedure disclosed herein. Usual procedures are used for opening the tissues and controlling bleeding by using bipolar coagulation, insertion of gel foam where necessary and protection of nerve roots and axilla using gel foam. Post-operative procedures involving packing, suturing the various layers of tissue, etc. are also usual and will not be discussed further herein.

Upon arrival at the operating site the dural and associated nerve roots are moved out of the way with known retractors. A bone chisel is used to cut a small groove in the superior and inferior surfaces 14 on adjacent vertebrae 11 and 12 on one side of the center line 17. A disc space spreader 21, such as that disclosed in U.S. patent application Ser. No. 09/329,096, Mehdizadeh, incorporated herein by reference, is inserted into the cut grooves with the spline 22 on the disc space spreader entering the grooves. As disclosed in the aforesaid disc space spreader application, the spreader is tapped into place by tapping on the free end of a detachable rod 23 until the spreader is positioned substantially as shown in FIG. 2 of the drawings. The splines 22 on the disc space spreader further cut and define the grooves in the surfaces 14 on adjacent vertebrae and the direction of the rod 23 is recorded. The direction of the rod 23 may be recorded by marking two coordinates 24 and 26 on drapes 27 lying on the patient and surrounding the operating site as seen in FIG. 1. Alternatively, the direction of the rod 23 may be recorded by means of marks placed with a sterile pen on surrounding tissue or bone structure. Representative marks are seen by the marks carrying the items numbers 28 and 29 in FIG. 1. The axis of the rod 23 is aligned so that it is substantially perpendicular to a line from each mark 28 and 29. With adjacent vertebrae 11 and 12 now being spread, the rod 23 is detached from the disc space spreader 21 as described in the disc space spreader application and removed from the operating site. Nerve root and dural are now moved out of the way on the opposite side of the spinal column center line 17. The beginning of grooves in both the superior and inferior surfaces 14 of adjacent vertabrae are cut with a chisel. The grooves on the opposite side are spaced slightly from the center line 17. A single tang nerve root retractor and protector 31 (hereinafter referred to as a Hamid retractor) is inserted into the intradiscal space with a single tang 32 entering the chiseled grooves on the opposite side. The Hamid retractor 31 is tapped into place as seen in FIG. 2. The Hamid retractor is described in full in U.S. Pat. No. 5,803,904, Mehdizadeh, and such disclosure is incorporated herein by reference. The Hamid retractor is inserted in a direction parallel to that detected and recorded for the disc space spreader rod 23. Note that the Hamid retractor single tang 32 is positioned toward the center line 17 of the spinal column and that the nerve root and dural are outside or positioned to the left of the Hamid retractor 31 as seen in FIG. 2. A reamer of known configuration is inserted through the Hamid retractor into the disc space surrounded by the adjacent surfaces 14 to remove damaged disc material and any other debris.

The prosthesis to be placed within the disc space will usually have some means thereon to retain the prosthesis temporarily until tissue is allowed to grow around and retain it in a permanent fashion. The prosthesis may have outside threads, as in the case of the Ray threaded fusion cage(TM), or it may be non-threaded having surface pins to contact the surfaces 14. Alternatively, it may be a plastic member carrying some means for temporary retention within the disc space. In the case of the threaded prosthesis, a tap is inserted into the disc space through the Hamid retractor and, as the tap passes the facet joint 16, the inner edge of the facet joint is threaded thereby. With reference to FIG. 2, it may be seen that as the tap is moved through the Hamid retractor 31 toward the intradiscal space surrounded by the surfaces 14, it will touch the inner edge of the inferior facet 18. Following formation of the opposing surfaces 14 surrounding the disc space, the tap is removed through the Hamid retractor 31 and a threaded cage 33 is inserted into the disc space through the Hamid retractor and turned while engaged with the threads on the surfaces 14 to assume the position shown in FIG. 3. The threaded cage is guided into position by the threaded inner edge of the facet joint 16 and by the Hamid retractor 31. The Hamid retractor is aligned in a direction substantially parallel with the recorded direction for the disc space spreader rod 23 as described hereinbefore. The entry for the threaded cage 33 may be counter sunk about 2 mm. as seen at 34 to avoid any post-operative contact between the proximate end of the threaded cage 33 and the dural or nerve roots. The cage insertion handle is removed along with the Hamid retractor following positioning of the threaded cage 33.

Rod 23 is once again engaged with the disc space spreader 21 and the disc space spreader is removed from the position seen in FIG. 2. The Hamid retractor 31 is positioned in place of the disc space spreader on the one side so that the edges of the single tang 32 on the Hamid retractor enter the grooves formed by the splines 22 in the opposing surfaces 14. The Hamid retractor 31 therefore assumes a mirror image position to that seen in FIG. 2 with respect to the center line 17. With the Hamid retractor positioned as described, the nerve root and dural are again outside the retractor, in this instance to the right of the retractor in mirror image position to that seen in FIG. 2. A known reamer is inserted through the Hamid retractor into the disc space surrounded by the surfaces 14 to remove damaged disc material and any other debris. A tap is inserted through the Hamid retractor to form the surfaces 14 on opposite sides of the disc space. Upon removal of the tap a threaded cage is inserted through the Hamid retractor into the disc space to contact the threads formed therein. The threaded cage is guided by the threaded inner surface of the facet joint 16 and the Hamid retractor to assume a position represented by item 37 in FIG. 1. Again, the entry for threaded cage 37 into the intradiscal space may be countersunk about 2 mm. for purposes hereinbefore described. The direction of insertion of the threaded cage 37 is substantially parallel to the insertion direction of threaded cage 33 by aligning the Hamid retractor 31 with the recorded alignment marks 24 and 26 or 28 and 29. As a result, the two threaded cages 33 and 37 are inserted in parallel orientation within the intradiscal space surrounded by the surfaces 14 quite close to the center line 17 and separated only by about the width of the single tang 32 on the Hamid retractor. The laminectomy procedure is concluded in routine fashion by the operating surgeon.

The foregoing described laminectomy procedure is intended to be used for surgery performed inside the disc space surrounded by the surfaces 14 on the vertebrae and for placement of prostheses in the intadiscal space and spinal channel.

Although the best mode contemplated for carrying out the present invention has been shown and described herein, it will be understood that modification and variation may be made without departing from what is regarded to be the subject matter of the invention.

What is claimed:

1. A posterior approach laminectomy procedure for placing a prosthesis within the intradiscal space between adjacent vertebrae, comprising the steps of retracting the nerve root and dural, inserting a disc space spreader within the intradiscal space, recording the direction of the disc space spreader insertion, inserting a single tang retractor within the intradiscal space in a direction substantially parallel to the disc space spreader recorded direction, forming surfaces on the adjacent vertebrae to receive the prosthesis, and positioning the prosthesis in contact with the formed surfaces using the single tang retractor as a guide.

2. The laminectomy procedure of claim 1 wherein the prosthesis is a first fusion cage and a second fusion cage and the step of positioning pertains to positioning the first fusion cage, and further comprising the steps of removing the disc space spreader and the single tang retractor, inserting the single tang retractor within the intradiscal space in the position vacated by the removed disc space spreader and in a direction substantially parallel to the disc space spreader recorded direction, and placing the second fusion cage in contact with the formed surfaces using the single tang retractor as a guide.

3. A posterior approach laminectomy procedure for placing a prosthesis into the space between adjacent vertebrae, comprising the steps of retracting the dural to an out of the way position, spreading the adjacent vertebrae, inserting a single tang retractor into the space between adjacent vertebrae, recording the single tang retractor direction of insertion, forming opposing surfaces on the adjacent vertebrae to receive the prosthesis using the single tang retractor as a guide, and positioning the prosthesis between the opposing surfaces along the single tang insertion direction.

4. The posterior approach laminectomy procedure of claim 3 wherein the prosthesis is a threaded fusion cage, and wherein the step of forming comprises forming threads on the opposing surfaces and on the inner edge of the facet joint, and engaging the threads on the opposing vertebral surfaces with the threaded fusion cage.

5. The posterior approach laminectomy procedure of claim 4 comprising the step of using the single tang retractor and inner edge of the facet joint as guides during the step of positioning.

6. A posterior approach laminectomy procedure for placing a split prosthesis having a first half and a second half within the intradiscal space between adjacent vertebrae in positions on one side and an opposite side respectively of the spinal column center line, comprising the steps of retracting the nerve root and dural, inserting a disc space spreader within the intradiscal space on the one side, recording the direction of the disc space spreader insertion, inserting a single tang retractor within the intradiscal space on the opposite side in a direction substantially parallel to the disc space spreader recorded direction, forming surfaces on the adjacent vertebrae on the opposite side to receive the prosthesis second half, positioning the prosthesis second half in contact with the formed surfaces on the opposite side using the single tang retractor as a guide, removing the single tang retractor from the opposite side and the disc space spreader from the one side, inserting the single tang retractor within the intradiscal space on the one side in the position vacated by the disc space spreader and substantially parallel with the disc space spreader recorded direction, forming surfaces on the adjacent vertebrae on the one side to receive the prosthesis first half, positioning the prosthesis first half in contact with the formed surfaces on the one side using the single tang retractor as a guide, and removing the single tang retractor from the one side.

7. The laminectomy procedure of claim 6, wherein the first and second halves of the split prosthesis are threaded members, and wherein the steps of forming on the one side and the opposite side comprise the steps of forming threads on the surfaces.

* * * * *